(12) United States Patent
Knuebel

(10) Patent No.: US 11,367,510 B2
(45) Date of Patent: Jun. 21, 2022

(54) METHOD AND DATA PROCESSING DEVICE FOR THE COMPUTER-ASSISTED DETERMINATION OF A HAIR DYEING AGENT FOR DYEING HAIR IN A DESIRED HAIR COLOR AND DEVICE FOR PRODUCING AN INDIVIDUALLY DETERMINED HAIR DYEING AGENT

(71) Applicant: Henkel AG & Co. KGaA, Duesseldorf (DE)

(72) Inventor: Georg Knuebel, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 778 days.

(21) Appl. No.: 16/062,545

(22) PCT Filed: Dec. 16, 2016

(86) PCT No.: PCT/EP2016/081366
§ 371 (c)(1),
(2) Date: Jun. 14, 2018

(87) PCT Pub. No.: WO2017/103056
PCT Pub. Date: Jun. 22, 2017

(65) Prior Publication Data
US 2018/0357390 A1    Dec. 13, 2018

(30) Foreign Application Priority Data
Dec. 16, 2015   (DE) ............... 10 2015 225 459.3

(51) Int. Cl.
*G16C 20/30*      (2019.01)
*A45D 44/00*      (2006.01)
(Continued)

(52) U.S. Cl.
CPC ............. *G16C 20/30* (2019.02); *A45C 5/02* (2013.01); *A45D 44/005* (2013.01); *G06N 7/00* (2013.01);
(Continued)

(58) Field of Classification Search
CPC ............... G16C 20/30; A45D 44/005; A45D 2044/007; G06N 7/00
(Continued)

(56) References Cited

U.S. PATENT DOCUMENTS

2004/0000015 A1   1/2004  Grossinger
2006/0033907 A1*  2/2006  Inzinna, Jr. ............ G01J 3/462
                                                      356/45
2012/0080046 A1*  4/2012  Gross ................... A61K 8/4926
                                                      132/208

FOREIGN PATENT DOCUMENTS

EP    1374720 A1    1/2004
WO    0187245 A2    11/2001
(Continued)

OTHER PUBLICATIONS

EPO, International Search Report and Written Opinion issued in International Application No. PCT/EP2016/081366, dated Feb. 9, 2017.

*Primary Examiner* — Thomas J Hong
(74) *Attorney, Agent, or Firm* — Lorenz & Kopf, LLP

(57) ABSTRACT

A method and data processing device is described herein for computer-aided determination of a hair coloring agent for coloring of hair in a desired hair color. A device for production of an individually determined hair coloring agent is also described herein.

20 Claims, 5 Drawing Sheets

(51) Int. Cl.
  *A45C 5/02*    (2006.01)
  *G06Q 30/02*   (2012.01)
  *G06Q 30/06*   (2012.01)
  *G06N 7/00*    (2006.01)
  *G16H 20/10*   (2018.01)
  *G16H 50/20*   (2018.01)

(52) U.S. Cl.
  CPC ..... *G06Q 30/0281* (2013.01); *G06Q 30/0623* (2013.01); *G06Q 30/0631* (2013.01); *A45D 2044/007* (2013.01); *G16H 20/10* (2018.01); *G16H 50/20* (2018.01)

(58) Field of Classification Search
  USPC ........................................................ 434/100
  See application file for complete search history.

(56) References Cited

FOREIGN PATENT DOCUMENTS

| WO | 2006090363 A1 | 8/2006 |
|----|---------------|--------|
| WO | 2011024160 A1 | 3/2011 |
| WO | 2012127429 A2 | 9/2012 |

\* cited by examiner

FIG. 1

| Product | dE00 (12HW) | p-toluylenediamine sulphate [µmol / 100g] | m-aminophenol [µmol / 100g] |
|---|---|---|---|
| N&E 542 Medium Ash Blonde | 2.7 | 859.5 | 130.6 |
| N&E 545 Medium Golden Blonde | 1.4 | 1369.6 | 75.6 |
| N&E 550 Dark Blonde | 2.4 | 862.4 | 56.4 |
| N&E 555 Dark Golden Blonde | 2.7 | 989.6 | 72.9 |
| N&E 557 Multi Reflex Brown | 1.8 | 1959.6 | 0.0 |
| N&E 560 Light Brown | 2.8 | 2117.1 | 400.9 |
| N&E 562 Light Ash Brown | 2.9 | 1505.7 | 184.5 |
| N&E 565 Light Golden Brown | 2.0 | 1811.9 | 166.3 |
| N&E 566 Cinnamon Golden Brown | 1.6 | 3453.3 | 234.0 |
| N&E 568 Intense Red | 3.4 | 0.0 | 2000.1 |
| N&E 570 Medium Brown | 1.8 | 2650.1 | 422.7 |
| N&E 574 Bittersweet Chocolate | 1.6 | 3861.9 | 0.0 |
| N&E 576 Chestnut Red Brown | 1.4 | 2810.3 | 304.3 |
| N&E 580 Dark Brown | 2.3 | 3759.4 | 989.7 |
| N&E 584 Mocca Chocolate | 1.4 | 3595.9 | 384.9 |
| N&E 585 Multi Reflex Brown | 1.9 | 2928.5 | 229.1 |
| N&E 586 Cinnamon Dark Brown | 1.3 | 5616.1 | 0.0 |
| N&E 588 Glossy Acai Berry | 3.1 | 1999.3 | 0.0 |
| N&E 590 Black | 0.5 | 6475.1 | 916.4 |
| Nectra 688 | 2.2 | 0.0 | 2776.8 |
| Nectra 499 | 1.9 | 447.2 | 386.7 |
| Nectra 568 | 1.9 | 1804.8 | 491.7 |
| Nectra 400 | 1.8 | 4133.9 | 1090.5 |
| Syoss Oleo 3-10 | 2.3 | 3759.4 | 989.7 |
| Syoss Oleo 5-92 | 2.8 | 0.0 | 1963.9 |
| Nectra 300 | 1.1 | 5650.4 | 1484.6 |
| Nectra 468 | 1.4 | 2338.3 | 0.0 |
| Cashmere Red Variant 2 | 2.8 | 0.0 | 0.0 |
| Syoss Color 2014 5-22 | 2.8 | 491.7 | 2812.0 |
| Syoss Color 2014 1-4 | 2.1 | 4994.3 | 0.0 |
| Syoss Color 2014 5-28 | 1.7 | 1736.7 | 165.0 |
| Syoss Oleo 4-29 | 4.4 | 681.3 | 227.7 |
| Syoss Oleo 1-40 | 2.5 | 4994.3 | 0.0 |
| Igora Royal 5-88 | 2.8 | 491.7 | 2812.0 |
| Nectra 777 | 7.4 | 0.0 | 630.0 |
| Igora Royal 3-0 | 2.2 | 5788.9 | 1512.1 |
| Igora Royal 5-5 | 1.7 | 2043.1 | 165.0 |
| Igora Royal 6-65 | 1.8 | 1793.4 | 183.3 |
| Igora Royal 6-0 | 2.9 | 1922.6 | 440.3 |
| Igora Royal 6-1 | 3.7 | 1566.4 | 247.4 |
| Igora Royal 4-88 | 2.6 | 794.6 | 1374.6 |
| Igora Royal 7-887 | 2.2 | 149.8 | 0.0 |
| Syoss Color 2012 4-2 | 4.1 | 1589.1 | 458.2 |
| Syoss Color 2012 5-22 | 2.8 | 612.9 | 481.1 |
| Syoss Color 2012 1-4 | 2.4 | 4994.3 | 0.0 |
| Syoss Color 2012 5-29 | 3.2 | 0.0 | 2000.1 |
| Syoss Color 2012 3-65 | 1.3 | 3904.7 | 412.4 |
| Syoss Color 2012 5-0 | 1.9 | 3132.8 | 710.2 |
| Brillance 880 | 1.5 | 3408.6 | 740.9 |
| Igora Royal 1-0 | 1.0 | 7355.3 | 733.1 |
| Syoss Oleo 2-10 | 1.8 | 5012.5 | 1319.6 |
| Syoss Oleo 4-18 | 2.6 | 2042.9 | 181.5 |
| Syoss Oleo 6-10 | 2.4 | 2144.4 | 163.1 |

METHOD AND DATA PROCESSING DEVICE FOR THE COMPUTER-ASSISTED DETERMINATION OF A HAIR DYEING AGENT FOR DYEING HAIR IN A DESIRED HAIR COLOR AND DEVICE FOR PRODUCING AN INDIVIDUALLY DETERMINED HAIR DYEING AGENT

CROSS-REFERENCE TO RELATED APPLICATION

This application is a U.S. National-Stage entry under 35 U.S.C. § 371 based on International Application No PCT/EP2016/081366, filed Dec. 16, 2016 which was published under PCT Article 21(2) and which claims priority to German Application No. 10 2015 225 459.3, filed Dec. 16, 2015, which are all hereby incorporated in their entirety by reference.

TECHNICAL FIELD

The present disclosure relates to a method and a data processing device for computer-aided determination of a hair coloring agent for coloring of hair in a desired hair color and a device for production of an individually determined hair coloring agent.

BACKGROUND

With conventional methods for determination of a hair coloring agent for the coloring of hair in a desired hair color, end customers typically only have a few values available to choose from for definition of an original state of the hair to be colored, for example, the base hair color, a degree of graying or a degree of damage, including, for example, three values for the base hair color (e.g. blond, medium-blond and brown), three values for the degree of graying (about 0%, about 50% and about 100%) and three values for the degree of damage (no damage, light damage, heavy damage).

However, this only enables determination of an expected coloring result for a maximum of one case in which an original state of the hair of a person coincidentally correspond exactly to an available combination of values available to choose from for determination of an original state (e.g. blond, about 50% and light damage).

For a person who would like to color their hair (have their hair colored), however, it is very important that the expected result matches the achieved coloring result.

BRIEF SUMMARY

This disclosure provides a method for computer-aided determination of a hair coloring agent for the coloring of hair in a desired hair color. The method includes determining a value and/or of values for at least one initial state parameter describing an initial state of the hair to be colored; determining a plurality of hair colors achievable by coloring with an available hair coloring agent, based on a relationship between a plurality of coloring pre-condition parameters and achieved hair colors determined on the basis of hair color data for a plurality of coloring processes, wherein the plurality of coloring pre-condition parameters influences the respective coloring process, and the achieved hair colors are achieved by the respective coloring process, and the value and/or the values for the at least one initial state parameter; selecting the desired hair color from the plurality of hair colors achievable by an available hair coloring agent; and determining the hair coloring agent for the coloring of hair in the desired hair color based on the desired hair color and the determined relationship between the coloring pre-condition parameters and the achieved hair color.

BRIEF DESCRIPTION OF THE DRAWINGS

The present disclosure will hereinafter be described in conjunction with the following drawing figures, wherein like numerals denote like elements, and:

FIG. 1 shows hair color data according to an exemplary embodiment;

DETAILED DESCRIPTION

Figure 2:
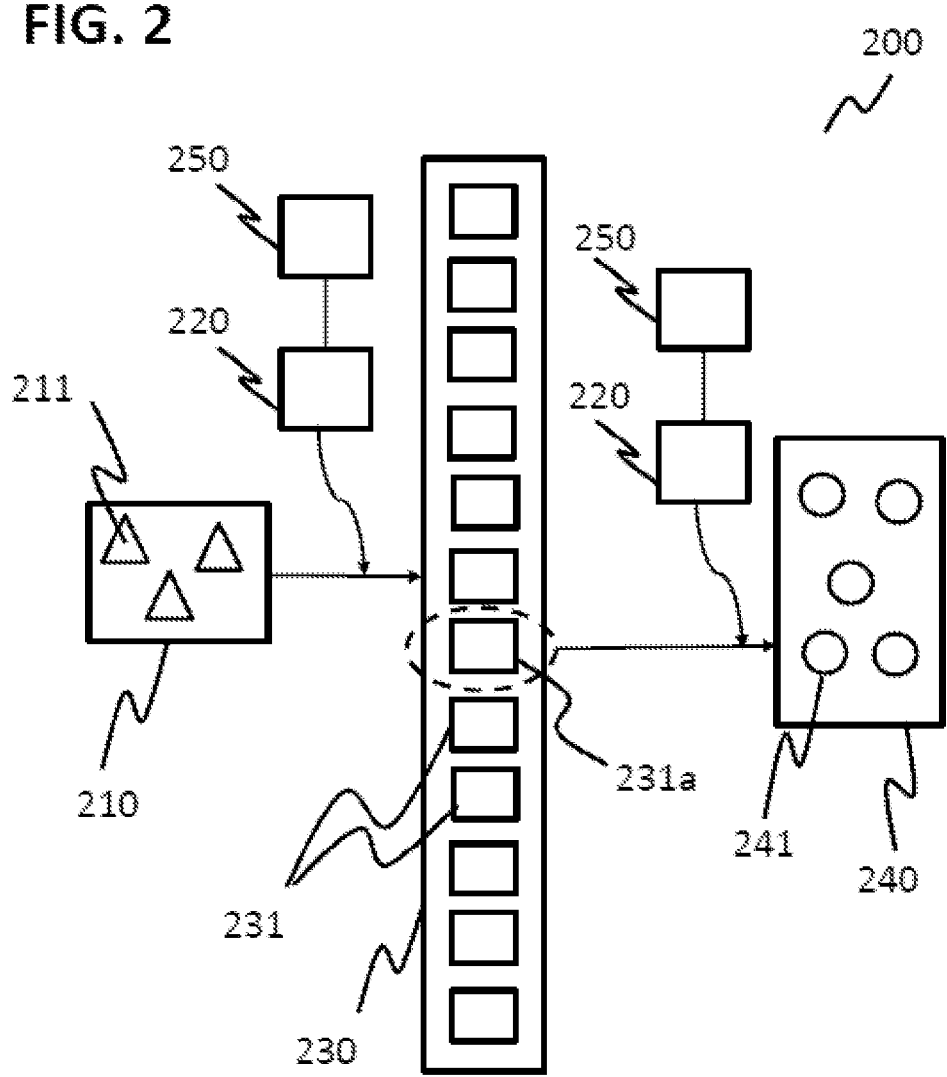
FIG. 2 shows a schematic representation of a method for computer-aided determination of a hair coloring agent for coloring of hair in a desired hair color.

The following detailed description is merely exemplary in nature and is not intended to limit the disclosure or the application and uses of the subject matter as described herein. Furthermore, there is no intention to be bound by any theory presented in the preceding background or the following detailed description.

In various exemplary embodiments, a method is prepared in which an individual original state of the hair can be taken into consideration in determination of a hair coloring agent for the coloring of hair in a desired hair color. In the process, the original state of the hair can be determined, for example, by employing measurements.

In various exemplary embodiments, with the determination of the hair coloring agent for the coloring of hair in a desired hair color, desired values for additional properties of hair colors can also be taken into consideration.

In general, properties of hair colors can include, for example, hair color information (a color), fastness to washing, light fastness, gray coverage or additional properties. In the process, the hair colors can be created by employing dyeing hair with a hair coloring agent, which is also referred to as a dyeing process.

A "color" can be understood as an interaction of a shade (i.e. a spectral color impression, also referred to as a hue, which can be understood as what is considered the "actual color"), a color intensity (i.e. how intensively the color appears, e.g. compared with a neutral gray tone, which is also referred to as saturation, color saturation, chroma, chromaticity or depth of color) and a brightness (i.e. how light or dark the color appears).

In various exemplary embodiments, the color information can, for example, have a parameterization in a known color space, for example in a $L^*a^*b$ color space (wherein $L^*$ indicates the brightness of a color, $a^*$ the portion of green and red and $b^*$ the portion of blue and yellow of the color, where the abbreviated form Lab and/or individual L, a and/or b are used here) in an RGB color space with color portions in red, green and blue, in a CMYK color space with color portions in cyan, magenta, yellow and black or in any other arbitrary color space.

The term "shade" can be understood, as described above, to mean the spectral color impression of a color independently of how it can be parameterized, such as a point in a two-dimensional color space (e.g. a*b* of the L*a*b* system) or a ratio of color portions (such as in the RGB color space or in the CMYK color space).

In various exemplary embodiments, a color space from which the color information (e.g. the hair color information of the colored hair or the hair before the coloring, which is also referred to as the base hair color) arose, or in which the color information is represented (for example, if a hair color is represented, see below) can be procured so that a determined or represented color is independent of a medium through which the color is determined or represented (e.g. color measuring device, screen, printer, scanner, human eye, etc.). The color space can be, for example, an L*a*b* color space and the color information can, for example, be a shade parameterized by employing a* and b*. The uniform representation in the medium-independent color space can make it possible, for example, to present a close-to-reality coloring result to be expected, for example, in which the same color impression of a color achieved by coloring is left on the observer in a representation of the result to be expected, for example as printing on a package, an advertisement on a computer screen, etc.

Hair coloring agents can have a mixture of different dye precursors and/r or dyes and can thus also be referred to as a coloring mixture.

A prediction or the aforementioned properties of hair colors, i.e. a determination of a coloring result to be expected, without having to actually carry out the coloring process can be more difficult for hair coloring, i.e. the production of a hair color, than in related areas of color production, e.g. in photo printing, because dyes are not typically used for hair coloring, at least not directly, rather dye precursors. While a coloring process can include a multitude of different dyes, it is possible that their properties as pure substances are not known.

To determine expected hair colors for a (e.g. arbitrary) initial state and for a large number of combinations of relevant concentrations of a plurality of dye precursors, methods from the field of predictive analytics (also known as "big data", "data mining" or "machine learning can be used in order to enable precise calculations of properties of hair colors, such as color information, fastness to washing, gray coverage and/or light fastness, despite the many parameters.

The (e.g. arbitrary) initial state can, for example, have an arbitrary value for an initial state parameter or an arbitrary combination of values for a plurality of initial state parameters, e.g. for a continuous distribution of values for the at least one initial state parameter.

The large number of combinations of concentrations of the plurality of dye precursors can have, for example, about $10^5$ combinations or more, or, for example, a continuous distribution of values for the concentrations of the plurality of dye precursors.

A relationship between a plurality of coloring pre-condition parameters and at least one coloring result parameter can be determined by employing predictive analytics using hair color data. In the process, the plurality of coloring pre-condition parameters can have a plurality of concentrations of dye precursors and at least one initial state parameter.

It is now possible to guarantee a color result to a user (e.g. a consumer) that is as close as possible to their desired hair color (insofar as it is chemically possible) by employing the methods from predictive analytics.

In various exemplary embodiments, a method for computer-aided determination of a hair coloring agent for the coloring of hair in a desired hair color can be prepared.

In various exemplary embodiments, a value for at least one initial state parameter which describes an initial state of the hair to be colored can be determined. For example, a value can be determined for a plurality of initial state parameters in each case. The at least one initial state parameter can, for example, have at least one initial hair color of the hair to be colored, wherein the initial hair color can be parameterized in a color space, such as a L*a*b* color space, an RGB color space, etc.

In various exemplary embodiments, the at least one initial hair color can include a multitude of initial hair colors. The hair to be colored can, for example, include a multitude of initial hair colors. For example, a first initial hair color at the tips of the hair can be different from a second initial hair color at the base of the hair and/or a third initial color on a main portion of the hair, and/or a fourth initial color on strands of the hair, etc.

The at least one initial state parameter can also have a degree of graying of the hair, a degree of damage of the hair, etc., in addition to the initial hair color.

In various exemplary embodiments, an initial hair color can be selected from a plurality of initial hair colors, for example, by a person whose hair it is, as an initial hair color which is representative for the hair, such as an initial hair color which makes the greatest color impression on a person observing the hair.

In various exemplary embodiments, a plurality of hair colors achievable by coloring with an available hair coloring agent can be determined from a plurality of available hair coloring agents.

A relationship between a plurality of coloring pre-condition parameters and achieved hair colors, which is or was determined on the basis of hair color data for a plurality of coloring processes, and the at least one value for the at least one initial state parameter are based on the determination of the achievable hair colors in various exemplary embodiments.

In determining the achievable hair colors in various exemplary embodiments, at least one desired value for an additional (e.g. in addition to the hair color) color result parameter can be taken into consideration. For example, when determining the achievable hair colors, the achievable hair colors are limited to those which also have the (e.g. minimum) value for the at least one additional coloring result parameter, such as a required (minimum) fastness to washing or a required (minimum) gray coverage.

In various exemplary embodiments, the plurality of available hair coloring agents can have a plurality of prepackaged hair coloring agents, such as hair coloring agents which are commercially available. In various exemplary embodiments, the plurality of available hair coloring agents can include a plurality of hair coloring agents having a previously unknown, unused or uncolored combination of concentrations of dye precursors. In various exemplary embodiments, the plurality of available hair coloring agents can have both prepackaged and unknown hair coloring agents.

In various exemplary embodiments, the method can be executed by employing a data processing device.

The data processing device can, for example, be a computer or any other data processing device which is suitable to store and prepare data and execute the predictive analytics, i.e. any data processing device with an adequately large data memory and sufficiently powerful processor.

As described, predictive analytics can be used in order to determine a relationship between a plurality of coloring pre-condition parameter (which can influence a coloring result) and at least one coloring result parameter (which describes a coloring result) on the basis of hair color data which can include results from, if applicable, a large number of test colorings. The determined relationship, also referred to as a model, can be used in order to also determine combinations of coloring pre-condition parameters not available in the hair color data, such as for new coloring agents, i.e. coloring agents with a new combination of concentrations of dye precursors, at least one property of an achieved hair color, such as color, gray coverage, fastness to washing and/or light fastness. The plurality of achieved hair colors can form a totality or a part of totality of hair colors which are theoretically achievable for an arbitrary combination of coloring pre-condition parameters. The at least one value for the at least one initial state parameter can be used in order to select colors from the theoretically achievable hair colors which are still achievable in consideration of the at least one value for the initial parameter.

For example, with a dark-brown initial hair color (insofar as the hair was night lightened before the coloring), only such hair colors from the totality of theoretically achievable hair colors which are at least as dark as the dark-brown initial hair color can be achievable hair colors.

In various exemplary embodiments, a desired hair color can be selected from the achievable hair colors which can be achieved by employing a coloring process with a hair coloring agent.

The selection of the desired hair color can take place, for example, by selection according to a presentation of achievable hair colors in various exemplary embodiments. The achievable hair colors can, for example, be presented by employing a display device, e.g. a screen, e.g. a computer screen, or by employing another output device, such as a printer. With presentation, the achievable hair colors can be presented, for example, as colors. In the process, the hair colors can be parameterized, for example, in a medium-independent color space, e.g. in the L*a*b* color space, which enables a realistic representation of the achievable hair colors, or the hair colors can be transformed from a color space to a color space which is expected by the output device. In various exemplary embodiments, the reproduction of the colors themselves can be omitted. Instead, values for a respective parameterization in the color space, for example, can be specified.

In various exemplary embodiments, the selection can include input of the selection into a data processing device, i.e. a computer. In the process, the input device can have any type of input, such as touching a screen, clicking in a screen area with a mouse, entering information by employing a keyboard and a voice command.

In various exemplary embodiments, specification of a desired hair color can take place before the presentation of the achievable hair colors or even before determination of the achievable hair colors, for example, on the basis of their values for the parameterization in the color space or a presentation of such generally parameterized colors.

In such cases, selection of the desired hair color can take place automatically. Insofar as the predetermined desired hair color is one of the achievable hair colors, it can be selected automatically as a desired hair color.

If the actual desired hair color is not an achievable hair color, the presentation of the achievable hair colors comprises specification by the color difference (ΔE) from the actual desired hair color.

Moreover, in various exemplary embodiments, a tolerance range can be prepared, wherein the tolerance range can be a color difference from the desired hair color that is tolerated. Determination of the hair coloring agent for coloring of hair in the desired hair color can also be based on the tolerance range.

According to various exemplary embodiments, the tolerance range can be smaller than a human perception threshold for the color difference. In the process, the human perception threshold can be defined in a usual manner, such as a threshold at which an average viewer perceives a color difference, at which a trained/sensitive viewer perceives a color difference, or at which an insensitive viewer perceives a color difference.

In various exemplary embodiments, there can be a plurality of hair coloring agents which result in the desired hair color (with or without defined tolerance range) by coloring the hair. In such cases, the hair coloring agent can be selected arbitrarily, or additional criteria can be used to determine the hair coloring agent, such as a price for the hair coloring agent, an effect on the hair (e.g. whether and, if applicable, how heavily the hair coloring agent can damage the hair), an availability of the hair coloring agent, etc.

In various exemplary embodiments, with use of the selected desired hair color, a color difference between a plurality of pre-packaged hair coloring agents (which can also be referred to as retail products) and the desired hair color can be determined.

In various exemplary embodiments, the hair coloring agent for the coloring of hair in the desired hair color can be determined based on the desired hair color and the determined relationship between the coloring pre-condition parameters and the achieved hair color.

In various exemplary embodiments, the hair coloring agent having the smallest color difference from the desired hair color according to the relationship determined in consideration of the initial state parameters can be selected from the pre-packaged hair coloring agents as the hair coloring agent for coloring hair in the desired hair color.

Alternatively, the color difference can be weighted in various exemplary embodiments. If, for example, the exact hue (H) of the desired hair color should be more important than the exact lightness (L), ΔH should have a greater influence on the color difference ΔE than ΔL.

In various exemplary embodiments, the hair coloring agent having a smallest hue difference ΔH, lightness difference ΔL or chroma difference ΔC from the desired hair color according to the relationship determined in consideration of the initial state parameters can be selected from the pre-packaged hair coloring agents as the hair coloring agent for coloring hair in the desired hair color.

In various embodiments, when, for example, additional or alternative hair coloring agents to the pre-packaged hair coloring agents cannot also be used, the desired hair color can, descriptively expressed, be plugged into the relationship (the model) as an initial parameter in order to obtain an assigned coloring agent which produces the desired hair color with the coloring pre-condition parameters, such as a combination of coloring agent precursors.

The at least one coloring result parameter can also have additional properties of the colored hair color in various exemplary embodiments, such as light fastness, fastness to washing or capacity for gray coverage.

In various exemplary embodiments, the measuring data of the date record, i.e. the measured specifications of the hair color data, the properties of the hair color generated by coloring can be described (e.g. L*, a*, b* for the color, a fastness to washing, light fastness, gray coverage, etc.) by independent variables. The dependency of the dependent variables on independent variables (such as the concentrations of dye precursors, such as the concentrations as they are applied on the head ("on head")) can be modeled by employing complex mathematical mode, which can be found by employing the predictive analytics method. This means a relationship between the independent and the dependent variables (in other words, between the coloring pre-condition parameters and the coloring result parameters) can be determined by employing the predictive analytics method. For example, this can be expressed as:

$$L^*a^*b^*=f(c_1,c_2,c_3,\ldots,c_n),$$

wherein L*a*b denotes the color parameters, $c_n$ (n=1, ..., n, n>1) denotes concentrations of dye precursors. In the process, the function can be known analytically or not. If no analytical function is known, the values of the dependent variables (of the coloring result parameters) are also calculated by employing numerical algorithms.

In addition to dye precursors, dyes can also be used in hair coloring agents. Accordingly, $c_i$ can also denote concentrations of dyes.

Possible independent variables can be metric (cardinal), ordinal or categorial.

In various exemplary embodiments, the independent variables (the coloring pre-condition parameters) can be properties which influence the coloring result, for example the concentration of a respective dye precursor, the base hair color, damage condition and/or a degree of graying of the hair or similar.

In various exemplary embodiments, a model can be generated by employing predictive analytics which predicts the coloring result parameters (dependent variables, see examples above) as precisely as possible with specified coloring pre-condition parameters (independent variables, see examples above).

In various exemplary embodiments, independent variables can be identified by employing predictive analytics which do not have any or only an insignificant influence on the model. In other words, it may be the case that independent variables (coloring pre-condition parameters) are present in the hair color data, from which it could be assumed that they have an influence on the dependent variables (coloring result parameters), although this is not or is only insignificantly the case. These less-important variables can be identified by employing the predictive analytics method and, if applicable, disregarded in subsequent modelings with comparable pre-conditions.

The non-influential independent variables can, in various exemplary embodiments, be independent variables which do not generally have an insignificant influence and are only significant for a specific initial state or/and a specified desired hair color. As illustrative examples, there can be dye precursors which, for example, are not used or are only used in negligible concentrations at the most in order to produce a red tone, or a degree of graying can be irrelevant or less relevant for hair with a light-blond initial hair color for an achieved hair color.

With presence of non-influential independent variables (coloring pre-condition parameters), determination of a relationship between the plurality of coloring pre-condition parameters and at least one coloring result parameter (e.g. a hair color) can be carried without the non-influential coloring pre-condition parameter in various exemplary embodiments.

Predictive analytics can be generally described as a method for extracting information from large amounts of data and generating a model from said data which make it possible to also make predictions for values that are not part of the data set. Using a predictive analytics method, part of the data set can be typically used as a training data set (also referred to as a training set or training data). Based on this training data set, one or multiple models can be generated, which can be tested on the basis of data which is not part of the training data set, on the basis of the overall data, or on the basis of a specially selected part of the data.

For example, a determination measure $R^2$, a mean absolute error, a mean quadratic error, a standard deviation and/or a mean deviation can be used for evaluation of the model, i.e. determination of the adaptation quality.

The determination measure $R^2$ can correspond to a squared correlation coefficient for a linear regression model. It can be defined differently for a different model (a different relationship).

Various functions or methods can be used for modeling by employing predictive analytics according to different exemplary embodiments. In a simple case, for example, a multiple linear regression can be used. Better results can be typically achieved using multiple polynomic regressions, neuronal networks, support vector machines, decision trees (e.g. tree ensembles) or similar methods.

In various exemplary embodiments, a method for computer-aided determination of a hair coloring agent for the coloring of hair in a desired hair color can have sequence according to the following (a so-called workflow):

1. determination of an initial hair color of a user (e.g. a consumer), e.g. on different portions of their hair (e.g. the hairstyle), e.g. base and tips of the hair, particularly on a portion of the hair estimated to be representative by the user;
2. determination (e.g. classification) of additional relevant initial state parameters, e.g. hair damage (degree of damage) and/or a degree of graying;
3. determination of a desired result (desired hair color) of the user, such as a combination of values in the L*a*b* color space;
4. calculation of a plurality of hair colors which are achievable, for example, on hair portions estimated to be representative by employing all available pre-packaged coloring agents (e.g. available in retail or from a hairdresser (retail products));
5. determination (e.g. calculation) of a color difference ΔE for all combinations of achievable hair color and desired hair color; and
6. selection of the pre-packaged coloring agent with the smallest color difference ΔE.

In various alternative exemplary embodiments, a method for computer-supported determination of a hair coloring agent for the coloring of hair in a desired hair color can be limited for the hair coloring agent to include an existing portfolio of (prepackaged) hair coloring agents (and/or their recipes) as well as all feasible recipes in a specified n-dimensional dye space (with n dye precursors) with comprehensive permutation of all theoretical dye precursor combinations and to calculate a color result (e.g. a plurality of achievable hair colors) on an initial position (e.g. a plurality of initial parameters) of the user. The method can include a sequence according to the following:

1. determination of an initial hair color of a user (e.g. a consumer), e.g. on different portions of their hair (e.g. the hairstyle), e.g. base and tips of the hair, particularly on a portion of the hair estimated to be representative by the user;
2. determination (e.g. classification) of additional relevant initial state parameters, e.g. hair damage (degree of damage) and/or a degree of graying;
3. determination of a desired result (desired hair color) of the user, such as a combination of values in the L*a*b* color space;
4. Identification of highly-relevant and less-relevant dyes (e.g. dye precursors) in a predictive analytics model (this can also be referred to as "feature selection");
5. simulation of a large number (e.g. >> about $10^5$) of theoretical recipes on the representative hair color (a base hair color which is a hair portion estimated to be representative) of the user;
6. determination (e.g. calculation) of a color difference $\Delta E$ for all combinations of achievable hair color and desired hair color; and
7. selection of the theoretical recipe with the smallest color difference $\Delta E$ as the hair coloring agent;
8. production according to this exact recipe, such as on special production lines or directly at the place of purchase (also referred to as point of sale).

Alternatively to the color state $\Delta E$, the hue difference $\Delta H$, the lightness difference $\Delta L$ or the chroma difference $\Delta C$ can also be taken into consideration in the method.

This embodiment can be very important for realization of a customized mass-production strategy (also referred to as mass customization strategy) in the hair coloring field.

In various exemplary embodiments, a method for computer-aided determination of a hair coloring agent for the coloring of hair in a desired hair color is prepared. The method can include: Determination of a value and/or of values for at least one initial state parameter which describes an initial state of the hair to be colored, determination of a plurality of hair colors achievable by coloring with an available hair coloring agent based on a relationship between a plurality of coloring pre-condition parameters determined on the basis of hair color data for a plurality of coloring processes, wherein the plurality of coloring pre-condition parameters influences the respective coloring process and the achieved hair colors are achieved by employing the respective coloring process and the value and/or the values for the at least one initial state parameter, selection of the desired hair color from the plurality of hair colors achievable by coloring with a respective available hair coloring agent, and determination of the hair coloring agent for coloring of hair in the desired hair color based on the desired hair color and the relationship determined between the coloring pre-condition parameters and the achieved hair colors.

According to various embodiments, determination of the hair coloring agent for coloring of hair in the desired hair color can include: Determination of a plurality of color differences, wherein each color difference can be a color difference the plurality of color differences between the desired hair color and a hair color calculated on the basis of the relationship for one of a plurality of pre-packaged hair coloring agents, determination of a minimum color difference from the plurality of color differences and determination of the pre-packaged hair coloring agent assigned to the minimum color difference as the hair coloring agent for coloring of hair in the desired hair color.

According to various embodiments, determination of the hair coloring agent for coloring of hair in the desired hair color can include: Determination, based on the desired hair color and use of the relationship determined between the plurality of coloring pre-condition parameters and the hair colors achieved from a combination of dye precursor concentrations, which arises according to the relationship in a coloring of the hair, wherein the combination of dye precursor concentrations can be a component of the hair coloring agent for coloring of hair in the desired hair color.

According to various embodiments, the at least one initial state parameter can have a base hair color.

According to various embodiments, the at least one initial state parameter also has at least one degree of graying and/or preliminary damage to the hair.

In accordance with various embodiments, the method can also include: Preparation of a tolerance range, wherein the tolerance range can be a color difference from the desired hair color which is tolerated, wherein determination of the hair coloring agent for coloring of hair in the desired hair color can also be based on the tolerance range.

In all of these embodiments, the color difference $\Delta E$ can be weighted with the hue difference $\Delta H$ and/or the lightness difference $\Delta L$.

According to various embodiments, the tolerance range can be smaller than a human perception threshold for the color difference.

In accordance with various embodiments, the method can also include: Preparation of a desired value for at least one additional coloring result parameter, determination of at least one achievable hair color which can have the desired value for the at least one additional coloring result parameter from the plurality of hair colors achievable by coloring with an available hair coloring agent, wherein selection of the desired hair color from the plurality of hair colors achievable by coloring with an available hair coloring agent can take place from the at least one achievable hair color which can have the desired value for the at least one additional coloring result parameter.

According to various embodiments, the at least one additional coloring result parameter can have a fastness to washing, light fastness and/or capacity for gray coverage.

In an advantageous variant of the method, the dye precursor concentrations and/or dye concentrations in the hair coloring agents can be predicted successively as follows:

For prediction of a first dye precursor concentration and/or dye concentration c1, the six color properties of the LAB color space of the initial hair color (L1, a1 and b1) and the desired hair color (L2, a2 and b2) are used. For prediction of a second dye precursor concentration and/or dye concentration c2, in addition to the six aforementioned color properties, the previously predicted dye precursor concentration and/or dye concentration c1 are used as an additional property. Accordingly, with prediction of a dye precursor concentration and/or dye concentration c3, in addition to the six aforementioned color properties, the previously predicted dye precursor concentration and/or dye concentration c1 and c2, etc. are used.

In a further advantageous variant of the method, the modeling takes place by employing predictive analytics using a tree ensemble model.

In various exemplary embodiments, a data processing device for execution of a computer-aided determination of a hair coloring agent for coloring of hair in a desired hair color is prepared, wherein the data processing device can be set up to execute the method described herein.

In various exemplary embodiments, a device for production of an individually determined hair coloring agent for coloring of hair in a desired hair color is prepared, comprising: a data processing device described herein and a hair coloring agent production device comprising a plurality of dye precursors and a dosing device for dosing the plurality of dye precursors, wherein a combination of dye precursor concentrations of the hair coloring agent can be determined by employing a method described herein, and wherein dosing of the plurality of dye precursors by employing the dosing device can take place based on the combination of dye precursor concentrations and the hair coloring agent.

In various embodiments, the device can be prepared at a point of sale for hair treatment products.

Exemplary embodiments of the present disclosure are shown in the figures and are explained in detail below.

The figures show the following:

FIG. 1 shows hair color data according to an exemplary embodiment.

Figure 3:
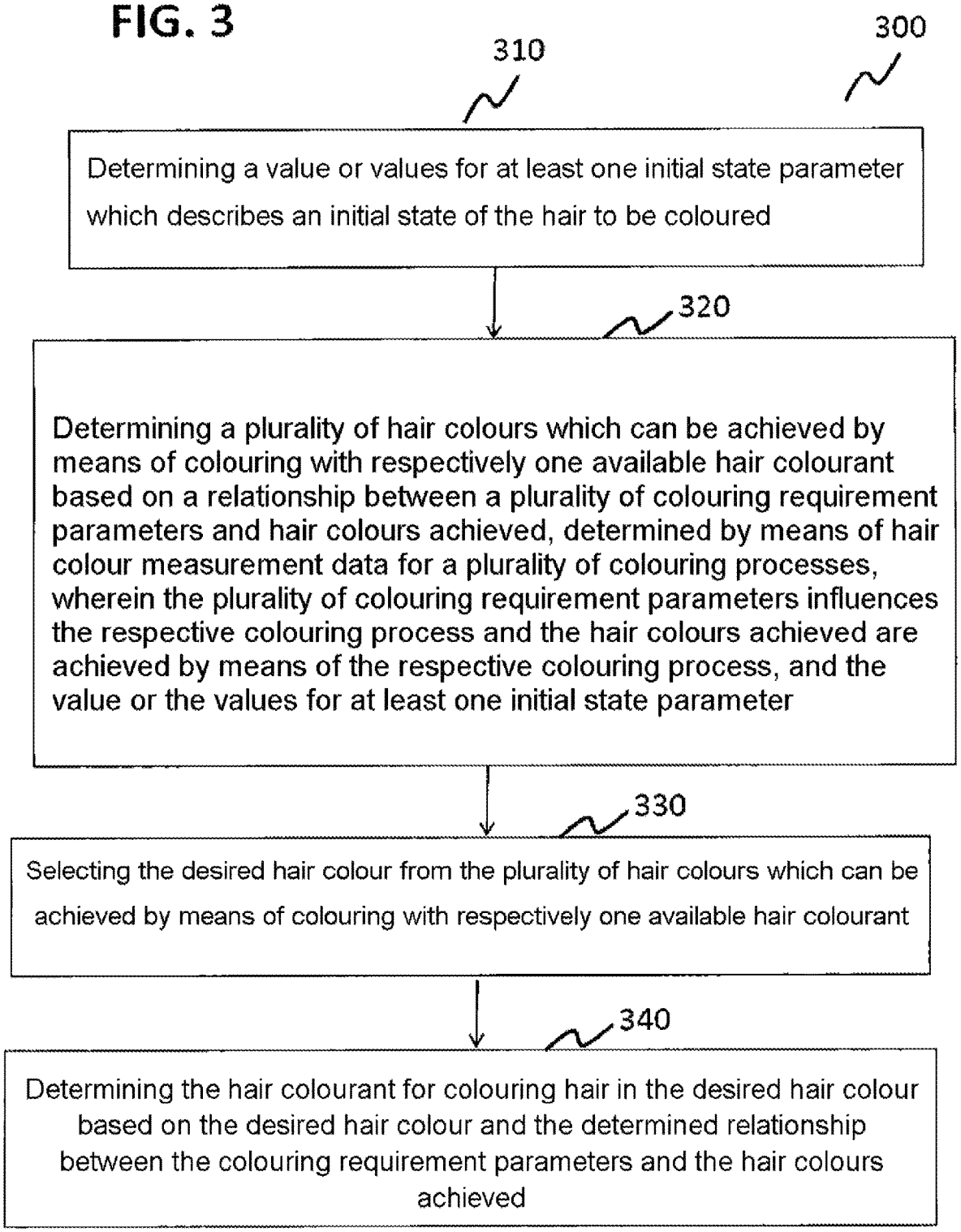
FIG. 3 shows a flow diagram which represents a method for computer-aided determination of a hair coloring agent for coloring of hair in a desired hair color according to various exemplary embodiments.
Figure 4:
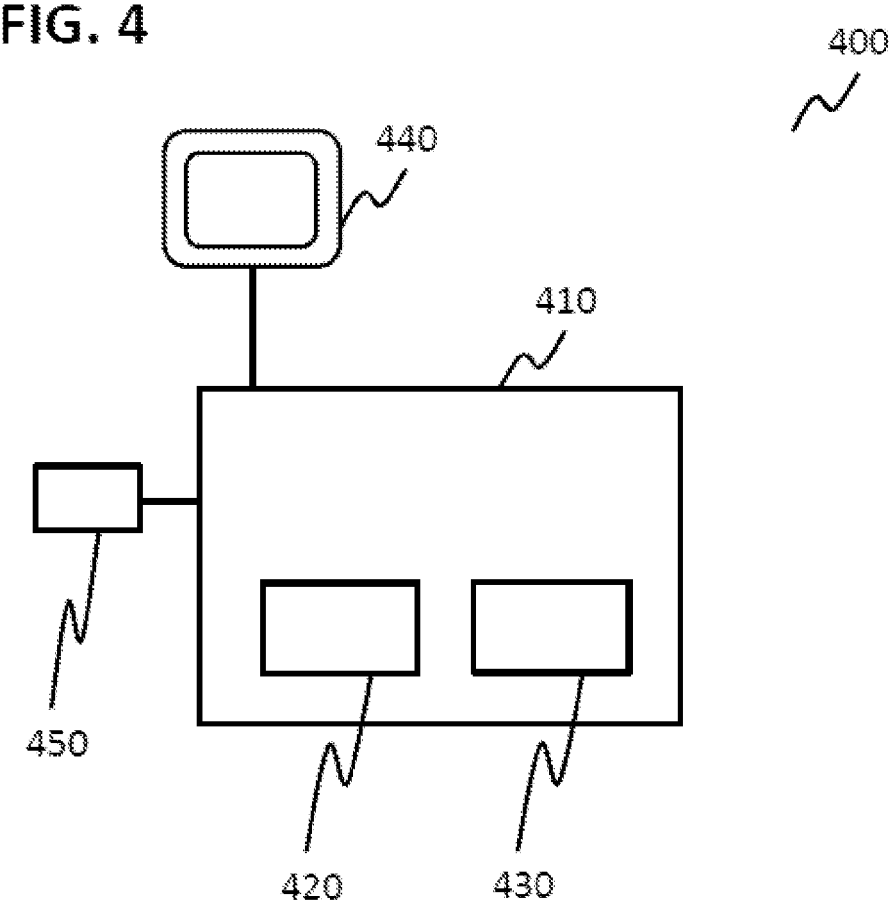
FIG. 4 shows a schematic representation of a data processing device according to various exemplary embodiments.
Figure 5:
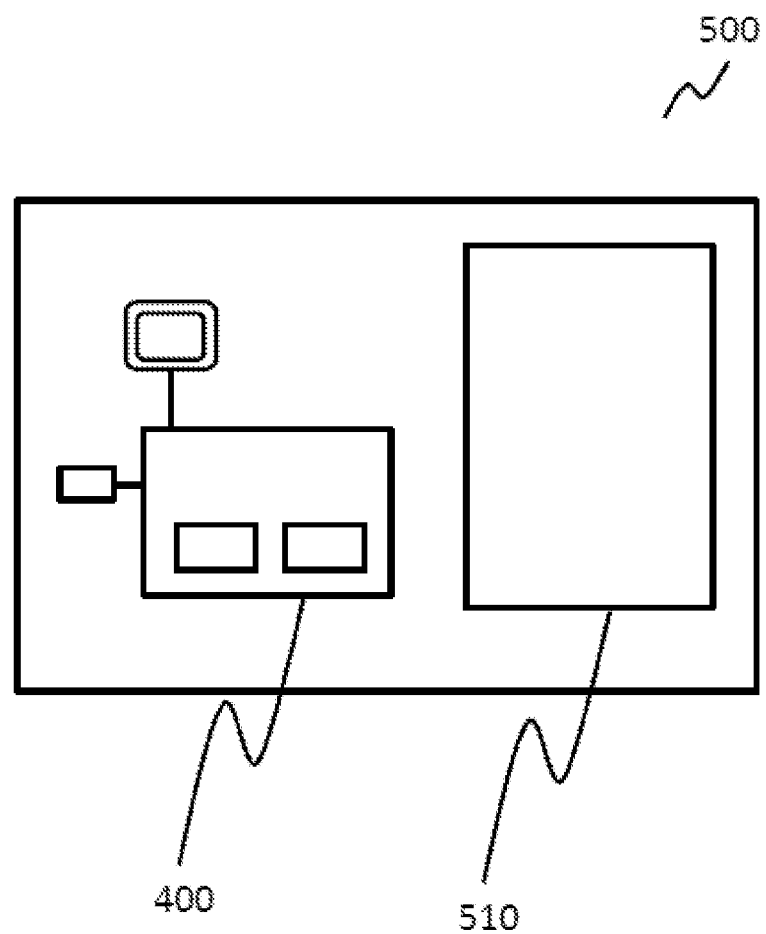
FIG. 5 shows a schematic representation of a device for production of an individually determined hair coloring agent for coloring of hair in a desired hair color according to the various exemplary embodiments.

FIG. 2 shows a schematic representation of a method for computer-aided determination of a hair coloring agent for coloring of hair in a desired hair color;

FIG. 3 shows a flow diagram which represents a method for computer-aided determination of a hair coloring agent for coloring of hair in a desired hair color according to various exemplary embodiments;

FIG. 4 shows a schematic representation of a data processing device according to various exemplary embodiments; and FIG. 5 shows a schematic representation of a device for production of an individually determined hair coloring agent for coloring of hair in a desired hair color according to the various exemplary embodiments.

In the following detailed description, reference is made to the attached drawings, which are part of the present application and show specific embodiments for clarification purposes in which the present disclosure can be implemented. It should be understood that other bodies can be used and structural or logical changes can be made without deviating from the scope of protection of the present disclosure. It should be understood that the features of the various exemplary embodiments described herein can be combined with each other, unless something different is specifically indicated. The following detailed description, therefore, should not have a limiting effect and the scope of protection of the present disclosure is defined by the appended claims.

FIG. 1 shows hair color data 100 according to an exemplary embodiment.

The hair color data 100 shows a multitude of coloring pre-condition parameters 130 (concentrations of the two dye precursors) and a coloring result parameter 120 (a color difference $\Delta E$ after about 12 washings of the hair) for a multitude of coloring processes (including two examples marked 110. An example value for one of the dye pre-condition parameters is marked 131. An example value for a coloring result parameter is marked 121. In addition to the parameters of the hair color data 100 shown here, the hair color data can also include values for at least one initial state parameter (not shown, such as a base hair color, a damage state, a degree of graying or similar).

The data presented in the tables is only exemplary for the purpose of clarification. The hair color data used for the method in various exemplary embodiments depends on a concrete application. For example, different, fewer or more products can be used, which, if applicable, can have different, more or fewer dye precursors or additional (partially-oxidizing) dyes and, in addition to the color, other parameters can be determined and specified in the hair color data, such as light fastness, a base hair color, etc.

Preparation of hair color data as a table is only exemplary. The hair color data can be provided in any form in which an assignment of coloring results to the respective color pre-condition parameters and use of a computer-aided use of hair color data are enabled.

FIG. 2 shows a schematic representation 200 of a method for computer-aided determination of a hair coloring agent for coloring of hair in a desired hair color.

In various exemplary embodiments, an initial state 210 can be prepared. The initial state 210 can include a value for at least one initial state parameter 211, for example, for a plurality of initial state parameters 211.

The at least one initial state parameter 211 can, for example, have at least one initial hair color of the hair to be colored, wherein the initial hair color can be parameterized in a color space, such as a L*a*b* color space, an RGB color space, etc.

In various exemplary embodiments, the at least one initial hair color can include a multitude of initial hair colors, for example, a first initial hair color on the tips of the hair, a second initial hair color on the base of the hair and/or a third initial hair color on a main portion of the hair, and/or a fourth initial hair color on strands of the hair, etc.

A representative hair color for the hair can, for example, be determined by the user.

The initial hair color can be determined in various exemplary embodiments by employing measuring, e.g. by employing a colorimetric measurement, for example, under defined conditions, e.g. with respect to the type of light, etc.

The at least one initial state parameter 211 can also have a degree of graying of the hair, a degree of damage of the hair, etc., in addition to the initial hair color.

In various exemplary embodiments, a plurality of hair colors 231 achievable by coloring with an available hair coloring agent can be determined from a plurality of available hair coloring agents.

The plurality of achievable hair colors 231 can form a totality 230 of achievable hair colors.

A relationship 220 between a plurality of coloring pre-condition parameters 250 and achieved hair colors 231, which is or was determined on the basis of hair color data for a plurality of coloring processes, and the at least one value for the at least one initial state parameter 211 are based on the determination of the achievable hair colors in various exemplary embodiments.

In determining the achievable hair colors 231 in various exemplary embodiments, at least one desired value for an additional (e.g. in addition to the hair color) color result parameter can be taken into consideration (not illustrated). For example, when determining the achievable hair colors 231, the achievable hair colors are limited to those which also have the (e.g. minimum) value for the at least one additional coloring result parameter, such as a required (minimum) fastness to washing or a required (minimum) gray coverage.

In various exemplary embodiments, the plurality of available hair coloring agents can include a plurality of pre-packaged hair coloring agents. In this case, the totality 230 of achievable hair colors can include discrete values of the achievable hair colors 231.

In various exemplary embodiments, the plurality of available hair coloring agents can include a plurality of hair coloring agents having a previously unknown, unused or uncolored combination of concentrations of dye precursors. In this case, the totality 230 of achievable hair colors can include a continuous distribution of achievable hair colors 231.

In various exemplary embodiments, the plurality of available hair coloring agents can have both prepackaged and unknown hair coloring agents.

In various exemplary embodiments, the method can be executed by employing a data processing device (see FIG. 4 and the corresponding description).

In various exemplary embodiments, a desired hair color 231a can be selected from the achievable hair colors 231 which can be achieved by employing a coloring process with a hair coloring agent.

The selection of the desired hair color 231a can include, for example, selection according to a presentation of achievable hair colors 231 in various exemplary embodiments.

Using the desired hair color 231a, the relationship (of the model) 220 and the color pre-condition parameter 250, the hair coloring agent 240 for coloring the hair in the desired hair color 231a can be determined. In the process, the hair coloring agent 240 can include a plurality of dye precursors 241 whose concentrations (and therefore a relative quantity ratio, e.g. a mixture ratio) are determined when determining the hair coloring agent 240.

In various exemplary embodiments, the hair coloring agent 240 can be any hair coloring agent 240 from a plurality of hair coloring agents which leads to a minimum color difference between the desired hair color and the hair color achieved by employing the hair coloring agent 240.

In various exemplary embodiments, predictive analytics can be executed by employing the software KNIME 2.11.2. Alternatively, any other software suitable for execution of the method can be used.

FIG. 3 shows a flow diagram 300 which represents a method for computer-aided determination of a hair coloring agent for coloring of hair in a desired hair color according to various exemplary embodiments.

In various exemplary embodiments, the method can include: Determination of a value and/or of values for at least one initial state parameter which describes (for 310) an initial state of the hair to be colored, determination of a plurality of hair colors achievable by coloring with an available hair coloring agent based on a relationship between a plurality of coloring pre-condition parameters determined on the basis of hair color data for a plurality of coloring processes, wherein the plurality of coloring pre-condition parameters influences the respective coloring process and the achieved hair colors are achieved by employing the respective coloring process and the value and/or the values for the at least one initial state parameter (for 320), selection of the desired hair color from the plurality of hair colors (for 330) achievable by coloring with a respective available hair coloring agent, and determination of the hair coloring agent for coloring of hair in the desired hair color based on the desired hair color and the relationship determined between the coloring pre-condition parameters and the achieved hair colors (for 340).

FIG. 4 shows a schematic representation of a data processing device 400 for execution of the method for determination of a hair coloring agent for coloring of hair in a desired hair color according to various exemplary embodiments.

The data processing device 400 can, for example, be a computer or any other data processing device which is suitable to store and prepare data and execute the predictive analytics, which executes the predictive analytics method and determines the desired hair color, i.e. any data processing device with an adequately large data memory and sufficiently powerful processor.

The data processing device 400 can have a processor 420 in various exemplary embodiments. The processor 420 can, for example, be a microprocessor of the data processing device 400 or have such a microprocessor.

In various exemplary embodiments, the data processing device 400 can have a data storage device 430. The data storage device can be an internal or external data storage device 430 of one of the aforementioned data processing devices 400 or have such a data storage device 430. The data storage device 430 can be set up to store data, such as hair color data or initial state parameters, which is saved and/or called up in execution of the method for determining a hair coloring agent for coloring hair in a desired hair color.

In various exemplary embodiments, the data processing device 400 can have a display device 440. The display device 440 can, for example, be a screen of a PC, a laptop or any another arbitrary data processing device 400. The display device 440 can be used, for example to reproduce the results of the method for determining a hair coloring agent for coloring of hair in a desired hair color, to query input parameters for execution of the method, or similar purposes.

In various exemplary embodiments, the data processing device 400 can have an input device 450 for provision of information to the data processing device 400, such as a keyboard, a mouse, contact-sensitive surface of the display device 440, etc.

FIG. 5 shows a schematic representation of a device 500 for production of an individually determined hair coloring agent for coloring of hair in a desired hair color according to the various exemplary embodiments.

The device 500 for production of an individually determined hair coloring agent for coloring of hair in a desired hair color can include a data processing device 400 (see FIG. 4 and corresponding description).

The device 500 can also include a hair coloring agent production device 510.

The hair coloring agent production device 510 can include a plurality of dye precursors and a dosing device for dosing of the plurality of dye precursors (not shown).

For production of the hair coloring agent, the dye precursors can be dosed on the basis of the determined dye precursor concentrations (for example, see FIG. 2 and the corresponding description, e.g. the dye precursors 241).

A combination of dye precursor concentrations of the hair coloring agent can be determined, for example, by employing a method as shown in FIG. 3 and the corresponding description.

The hair coloring agent production device 510 can be prepared in a production location for hair coloring agents in various exemplary embodiments. Alternatively, the hair coloring agent production device 510 can be prepared at a point of sale and/or place of use of hair coloring agents.

The preparation of the hair coloring agent production device 510 enables immediate production and preparation of an individually adapted hair coloring agent.

Additional advantageous variants of the method arise from the description of the device and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for computer-aided determination and outputting of a hair coloring agent for the coloring of hair in a desired hair color, comprising:
   determining, yin a processor, a value for at least one initial state parameter describing an initial state of the hair to be colored, the at least one initial state parameter comprising an initial hair color of the hair to be colored;
   determining, via the processor, a plurality of achievable hair colors that are achievable by coloring with one of a plurality of available hair coloring agents each having different combinations of concentrations of a plurality of dye precursors, based on a relationship between a plurality of coloring pre-condition parameters and achieved hair colors determined on the basis of hair color data for a plurality of coloring processes utilizing the plurality of available hair coloring agents, wherein the plurality of achievable hair colors are determined via the processor, based on both:
      the value for the at least one initial state parameter, including the initial hair color; and
      the different combinations of the plurality of dye precursors;
   outputting, via a computer output display device comprising a computer screen, a computer printer, or both, via instructions from the processor, the plurality of achievable hair colors;
   receiving, via a computer input device, a user selection of the desired hair color that is selected from the plurality of achievable hair colors;
   determining, via the processor, one of the plurality of hair coloring agents for the coloring of the hair in the desired hair color based on the desired hair color and the determined relationship between the coloring pre-condition parameters and the achieved hair color; and
   outputting the determined one of the plurality of hair color agents to the computer screen, the computer printer, or both, via instructions provided by the processor, and to a dosing device of a hair coloring production device for producing the determined one of the plurality of hair coloring agents for the coloring of the hair in the desired hair color by dosing of a combination of the plurality of dye precursors that corresponds to the one of the plurality of hair coloring agents for the desired hair color.

2. The method according to claim 1,
   wherein determining the hair coloring agent for coloring of hair in the desired hair color includes:
   determining a plurality of color differences, wherein each color difference of the plurality of color difference is a color difference between the desired hair color and a hair color calculation on the basis of the relationship for each of a plurality of pre-packaged hair coloring agents;
   determining a minimum color difference from the plurality of color differences; and
   determining pre-packaged hair coloring agent assigned to the minimum color difference as the hair coloring agent for coloring of hair in the desired hair color.

3. The method according to claim 1,
   wherein the at least one initial state parameter also includes at least a base hair color and a degree of preliminary damage to the hair.

4. The method according to claim 1, additionally comprising:
   preparing a tolerance range, wherein the tolerance range is a color difference from the desired hair color which is tolerated,
   wherein determination of the hair coloring agent for coloring of hair in the desired hair color is also based on the tolerance range.

5. The method according to claim 4,
   wherein the tolerance range is less than a threshold for the color difference which is perceptible to humans.

6. The method according to claim 1, additionally comprising:
   preparing a desired value for at least one additional coloring result parameter; and
   determining at least one achievable hair color which includes the desired value for the at least one additional coloring result parameter from the plurality of hair colors achievable by coloring with an available hair coloring agent,
   wherein selection of the desired hair color from the plurality of hair colors achievable by coloring with an available hair coloring agent takes place from the at least one achievable hair color having the desired value for the at least one additional coloring result parameter.

7. The method according to claim 6,
   wherein the at least one additional coloring result parameter includes a fastness to washing, light fastness and capacity for gray coverage.

8. The method according to claim 1,
   wherein determining the hair coloring agent for coloring of hair in the desired hair color includes:
   determining a plurality of color differences, wherein each color difference of the plurality of color difference is a color difference between the desired hair color and a hair color calculation on the basis of the relationship for each of a plurality of pre-packaged hair coloring agents;
   determining a minimum color difference from the plurality of color differences; and
   determining pre-packaged hair coloring agent assigned to the minimum color difference as the hair coloring agent for coloring of hair in the desired hair color,
   wherein the at least one initial state parameter includes a base hair color, and
   wherein the at least one initial state parameter also includes at least one degree of graying and/or preliminary damage to the hair.

9. The method according to claim 8, additionally comprising:
   preparing a tolerance range, wherein the tolerance range is a color difference from the desired hair color which is tolerated,
   wherein determination of the hair coloring agent for coloring of hair in the desired hair color is also based on the tolerance range.

10. The method according to claim 9,
    wherein the tolerance range is less than a threshold for the color difference which is perceptible to humans.

11. The method according to claim 10, additionally comprising:
    preparing a desired value for at least one additional coloring result parameter; and
    determining at least one achievable hair color which includes the desired value for the at least one additional coloring result parameter from the plurality of hair colors achievable by coloring with an available hair coloring agent,
wherein selection of the desired hair color from the plurality of hair colors achievable by coloring with an available hair coloring agent takes place from the at least one achievable hair color having the desired value for the at least one additional coloring result parameter.

12. The method according to claim 1, additionally comprising:
preparing a desired value for at least one additional coloring result parameter; and
determining at least one achievable hair color which includes the desired value for the at least one additional coloring result parameter from the plurality of hair colors achievable by coloring with an available hair coloring agent,
wherein selection of the desired hair color from the plurality of hair colors achievable by coloring with an available hair coloring agent takes place from the at least one achievable hair color having the desired value for the at least one additional coloring result parameter.

13. The method of claim 1, wherein the plurality of achievable hair colors are determined via the processor, using a tree ensemble model, based on both:
the at least one initial state parameter, including the initial hair color; and
the different combinations of the plurality of dye precursors.

14. A method for computer-aided production of a hair coloring agent for the coloring of hair in a desired hair color, comprising:
determining, yin a processor, a value for at least one initial state parameter describing an initial state of the hair to be colored, the at least one initial state parameter comprising an initial hair color of the hair to be colored;
determining, via the processor, a plurality of achievable hair colors that are achievable by coloring with one of a plurality of available hair coloring agents each having different combinations of concentrations of a plurality of dye precursors, based on a relationship between a plurality of coloring pre-condition parameters and achieved hair colors determined on the basis of hair color data for a plurality of coloring processes utilizing the plurality of available hair coloring agents, wherein the plurality of achievable hair colors are determined via the processor based on both:
the value for the at least one initial state parameter, including the initial hair color; and
the different combinations of the plurality of dye precursors;
automatically selecting, via the processor, the desired hair color from the plurality of achievable hair colors that most closely matches the initial hair color;
determining, via the processor, one of the plurality of hair coloring agents for the coloring of the hair in the desired hair color based on the desired hair color and the determined relationship between the coloring pre-condition parameters and the achieved hair color; and
producing the determined one of the plurality of hair coloring agents for the coloring of the hair in the desired hair color via a hair coloring production device, via instructions provided by the processor, by dosing of a combination of the plurality of dye precursors that corresponds to the selected one of the plurality of hair coloring agents for the desired hair color via a dosing device.

15. The method of claim 14, wherein the plurality of achievable hair colors are determined via the processor, using a tree ensemble model, based on both:
the at least one initial state parameter, including the initial hair color; and
the different combinations of the plurality of dye precursors.

16. A system for producing a hair coloring agent for the coloring of hair in a desired hair color, comprising:
a processor configured to:
determine a value for at least one initial state parameter describing an initial state of the hair to be colored, the at least one initial state parameter comprising an initial hair color of the hair to be colored;
determine a plurality of achievable hair colors that are achievable by coloring with one of a plurality of available hair coloring agents each having different combinations of concentrations of a plurality of dye precursors, based on a relationship between a plurality of coloring pre-condition parameters and achieved hair colors determined on the basis of hair color data for a plurality of coloring processes utilizing the plurality of available hair coloring agents, wherein the plurality of achievable hair colors are determined via the processor, based on both:
the value for the at least one initial state parameter, including the initial hair color; and
the different combinations of the plurality of dye precursors;
determine a desired hair color that is selected from the plurality of achievable hair colors; and
determine a selected one of the plurality of hair coloring agents for the coloring of the hair in the desired hair color based on the desired hair color and the determined relationship between the coloring pre-condition parameters and the achieved hair color; and
a hair coloring production device coupled to the processor and configured to produce the determined one of the plurality of hair coloring agents for the coloring of the hair in the desired hair color, via instructions provided by the processor, by dosing of a combination of the plurality of dye precursors that corresponds to the selected one of the plurality of hair coloring agents for the desired hair color via a dosing device.

17. The system of claim 16, wherein the processor is configured to automatically select the desired hair color from the plurality of achievable hair colors that most closely matches the initial hair color.

18. The system of claim 16 wherein the processor is configured to determine the desired hair color based on a user input comprising a user selection of the desired hair color that is selected from the plurality of achievable hair colors.

19. The system of claim 16, the processor is configured to determine the plurality of achievable hair colors using a tree ensemble model based on both:
the at least one initial state parameter, including the initial hair color; and
the different combinations of the plurality of dye precursors.

20. The system of claim 16, wherein the dosing device is configured to dose the plurality of precursors at a point of sale for hair treatment products.

* * * * *